(12) United States Patent
Van Der Schaar et al.

(10) Patent No.: US 9,235,141 B2
(45) Date of Patent: Jan. 12, 2016

(54) INSPECTION APPARATUS AND METHOD FOR MEASURING A PROPERTY OF A SUBSTRATE

(75) Inventors: Maurits Van Der Schaar, Eindhoven (NL); Arie Jeffrey Den Boef, Waalre (NL); Everhardus Cornelis Mos, Best (NL); Andreas Fuchs, Meerbusch (DE); Martyn John Coogans, Eindhoven (NL); Hendrik Jan Hidde Smilde, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 991 days.

(21) Appl. No.: 13/186,895

(22) Filed: Jul. 20, 2011

(65) Prior Publication Data
US 2012/0033193 A1 Feb. 9, 2012

Related U.S. Application Data

(60) Provisional application No. 61/371,282, filed on Aug. 6, 2010.

(51) Int. Cl.
*G03F 7/20* (2006.01)
*G01N 21/95* (2006.01)
*G01N 21/956* (2006.01)
*G03F 9/00* (2006.01)
*G01N 21/47* (2006.01)

(52) U.S. Cl.
CPC ........ G03F 7/70633 (2013.01); G01N 21/9501 (2013.01); G01N 21/95607 (2013.01); G03F 7/70616 (2013.01); *G01B 2210/56* (2013.01); *G01N 21/4788* (2013.01); *G03F 9/70* (2013.01)

(58) Field of Classification Search
CPC .......................... G03F 7/70633; G03F 7/70683
See application file for complete search history.

(56) References Cited

U.S. PATENT DOCUMENTS

| 5,173,380 | A | 12/1992 | Kamon | |
|---|---|---|---|---|
| 8,705,007 | B2 * | 4/2014 | Cramer et al. | 355/68 |

(Continued)

FOREIGN PATENT DOCUMENTS

EP 1 628 164 A2 2/2006

OTHER PUBLICATIONS

Lee, B. H., et al., "Diffraction-Based Overlay for Spacer Patterning and Double Patterning Technology", Proceedings of SPIE, Metrology, Inspection, and Process Control for Microlithography XXV, vol. 7971, pp. 79712U-1 to 79712U-10 (2011).

*Primary Examiner* — Peter B Kim
*Assistant Examiner* — Michelle Iacoletti
(74) *Attorney, Agent, or Firm* — Sterne, Kessler, Goldstein & Fox P.L.L.C.

(57) ABSTRACT

An inspection apparatus measures a property of a substrate including a periodic structure. An illumination system provides a beam of radiation with an illumination profile including a plurality of illuminated portions. A radiation projector projects the beam of radiation onto the substrate. A detector detects radiation scattered from the periodic structure and separately detects first order diffracted radiation and at least one higher order of diffracted radiation of each of the illuminated portions. A processor determines the property of the substrate from the detected radiation. The plurality of illuminated portions are arranged such that first order diffracted radiation arising from one or more of the illuminated portions are not overlapped by zeroth order or first order diffracted radiation arising from any other of the illuminated portions. Furthermore, the plurality of illuminated portions are arranged such that first order diffracted radiation arising from the one or more of the illuminated portions are overlapped by at least one of the higher orders of diffracted radiation arising from any other of the illuminated portions.

15 Claims, 12 Drawing Sheets

(56) References Cited

U.S. PATENT DOCUMENTS

| | | | |
|---|---|---|---|
| 8,786,825 B2 * | 7/2014 | Van De Kerkhof et al. | 355/67 |
| 2003/0143761 A1 * | 7/2003 | Fukuda | 438/7 |
| 2006/0033921 A1 | 2/2006 | Den Boef et al. | |
| 2006/0065625 A1 * | 3/2006 | Abdulhalim et al. | 216/59 |
| 2008/0198380 A1 * | 8/2008 | Straaijer et al. | 356/369 |
| 2010/0201963 A1 | 8/2010 | Cramer et al. | |

\* cited by examiner

INSPECTION APPARATUS AND METHOD FOR MEASURING A PROPERTY OF A SUBSTRATE

CROSS REFERENCE TO RELATED APPLICATIONS

This application claims the benefit under 35 U.S.C. 119(e) to U.S. Provisional Application No. 61/371,282, filed Aug. 6, 2010, which is incorporated by reference herein in its entirety.

FIELD

The present invention relates to methods of inspection and inspection apparatus usable, for example, in the manufacture of devices by lithographic techniques by a lithographic apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

Diffraction based scatterometry within the semiconductor industry is up until now used mainly for overlay and critical dimension (CD) measurements within metrology.

In angular resolved scatterometry, a periodic mark on a substrate is simultaneously illuminated at various angles. The light diffracted by this mark is used to measure particular characteristics of that mark. If the period of the mark is sufficiently large, the diffracted light will contain higher diffraction orders. However, part of the first diffraction order is often mixed with part of the zeroth diffraction order, as shown in accompanying FIG. 5. This overlap of diffraction orders generally yields a less robust reconstruction of the characteristics of the mark. In order to separate out the different diffraction orders annular illumination can be used, and this results in separated zeroth and first order diffraction patterns as shown in FIG. 6. However, it has been found that the use of such annular illumination may lead to errors in the measured mark characteristics since annular illumination provides less information in the diffracted light. For example, in annular illumination, there are no light beams near normal incidence that also contain information that is valuable for measuring the mark characteristics.

In typical scatterometers, it is a problem that illumination is limited to apertures that are suitable for small pitches, for example smaller than approximately 1000 nm, if separation of the individual orders is required with sufficient pixels in the separated orders.

It is desirable to characterize alignment targets and also overlay targets with large pitch with an angular resolved scatterometer. However, alignment targets normally have gratings with pitches larger than 1000 nm. This means that the known apertures do not (or only partly) separate the diffraction orders. For such large pitches, as well as the first diffraction order, higher diffraction orders such as the second third, etc. may be detected. It would be desirable to make separation of orders possible while keeping the number of detector pixels for these orders sufficiently large for accurate alignment target asymmetry reconstruction.

One of the assumptions that are commonly made with the overlay calculations and CD reconstructions are that of a symmetrical grating which is also uniform across the entire wafer. This assumption of symmetrical gratings has been found through experimental data to be incorrect and a more comprehensive understanding of these grating asymmetries has been found to be necessary to produce more accurate results. A number of lithographic and in-line processing variables can lead to asymmetry both within the upper and lower target grating of an overlay grating stack. These asymmetries are convoluted within in the output overlay result and can have contributions from the bottom target grating asymmetry, the top target grating asymmetry and the relative overlay between the two targets. It would be desirable to de-convolute these single grating asymmetries from the actual relative overlay.

Furthermore, more accurate knowledge of grating asymmetry distributions across the wafer is more and more desirable for process control within semiconductor manufacturing.

Grating asymmetry affects accuracy on alignment, overlay and critical dimension measurements in diffraction based scatterometry. Current methods to detect this are both time consuming and/or destructive.

Grating asymmetries and their distributions across the wafer are a good indicator of process variations caused by various semiconductor manufacturing steps, for example Chemical Mechanical Polishing (CMP) and etch. A fast and easy to use method of detecting this phenomena and it's variation across the wafer is desirable.

There is currently no known method to feed forward information of grating asymmetry and its distribution across the wafer.

There is currently no known method of accurately, quickly and non-destructively characterizing grating asymmetry and its distribution across the wafer.

SUMMARY

According to a first embodiment of the present invention, there is provided an inspection apparatus configured to measure a property of a substrate comprising a periodic structure. The apparatus comprises: an illumination system configured to provide a beam of radiation with an illumination profile comprising a plurality of illuminated portions, a radiation projector configured to project the beam of radiation onto the periodic structure,
a detector configured to detect radiation scattered from the periodic structure and separately detect first order diffracted radiation and at least one higher order of diffracted radiation of each of the illuminated portions, and a processor configured to determine the property of the substrate from the detected radiation. The plurality of illuminated portions are arranged such that at the detector first order diffracted radiation arising from at least one of the illuminated portions is not overlapped by zeroth order or first order diffracted radiation arising from any other of the illuminated portions.

According to a second embodiment of the present invention, there is provided a lithographic apparatus comprising: an illumination optical system arranged to illuminate a pattern, a projection optical system arranged to project an image of the pattern on to a substrate, and an inspection apparatus according to the first embodiment.

According to a third embodiment of the present invention, there is provided a lithographic cell comprising: a coater arranged to coat substrates with a radiation sensitive layer, a lithographic apparatus arranged to expose images onto the radiation sensitive layer of substrates coated by the coater, a developer arranged to develop images exposed by the lithographic apparatus, and an inspection apparatus according to above.

According to a fourth embodiment of the present invention, there is provided a method of inspection for measuring a property of a substrate comprising a periodic structure, the method comprising the following steps. Providing a beam of radiation with an illumination profile comprising a plurality of illuminated portions. Projecting the beam of radiation onto the periodic structure. Detecting radiation scattered from the periodic structure and separately detecting first order diffracted radiation and at least one higher order of diffracted radiation of each of the illuminated portions. Determining the property of the substrate from the detected radiation. The illuminated portions are arranged such that detected first order diffracted radiation arising from at least one of the illuminated portions is not overlapped by zeroth order or first order diffracted radiation arising from any other of the illuminated portions.

In one example, the periodic structure may comprise a single grating from which the radiation is scattered and the determining may comprise determining an asymmetry of the single grating from the difference between detected positive and negative first order diffracted radiation arising from the at least one of the illuminated portions.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the present invention and to enable a person skilled in the relevant art(s) to make and use the present invention.

Figure 1:
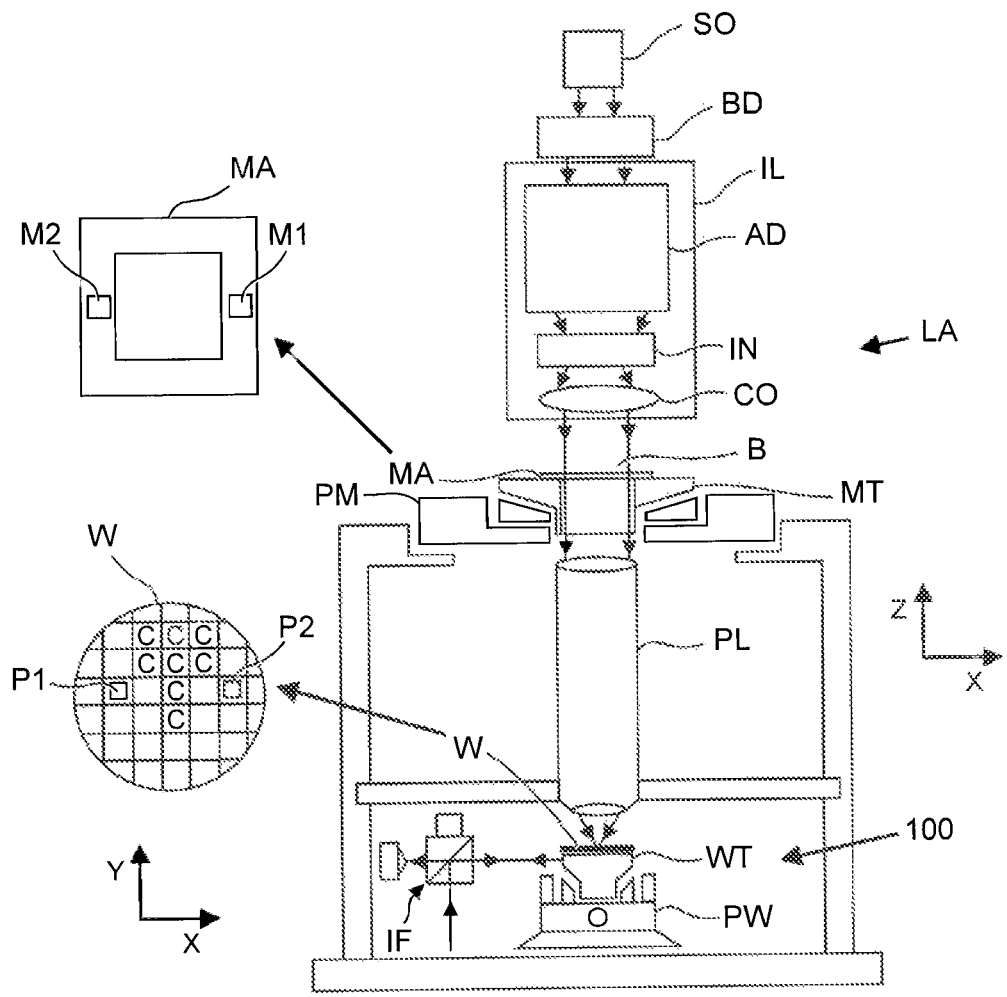
FIG. 1 depicts a lithographic apparatus.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the present invention. The scope of the present invention is not limited to the disclosed embodiment(s). The present invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

FIG. 1 schematically depicts a lithographic apparatus. The apparatus comprises an illumination system (illuminator) IL configured to condition a radiation beam B (e.g., UV radiation or DUV radiation), support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist-coated wafer) W and connected to a second positioner PW configured to accurately position the substrate in accordance with certain parameters, and a projection system (e.g., a refractive projection lens system) PL configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support stricture may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
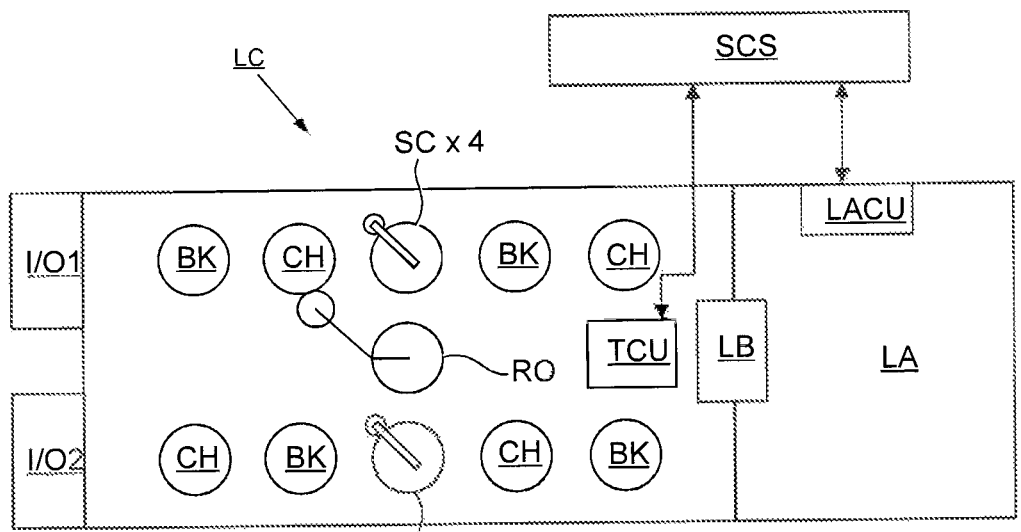
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
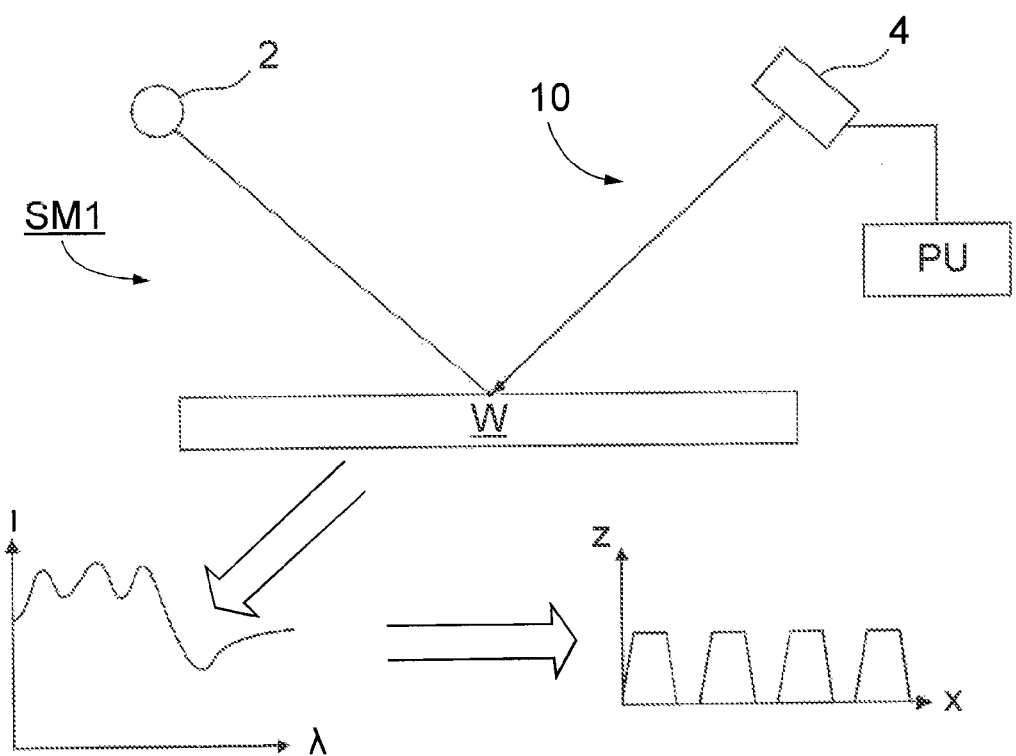
FIG. 3 depicts a first scatterometer.

FIG. 3 depicts a scatterometer. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
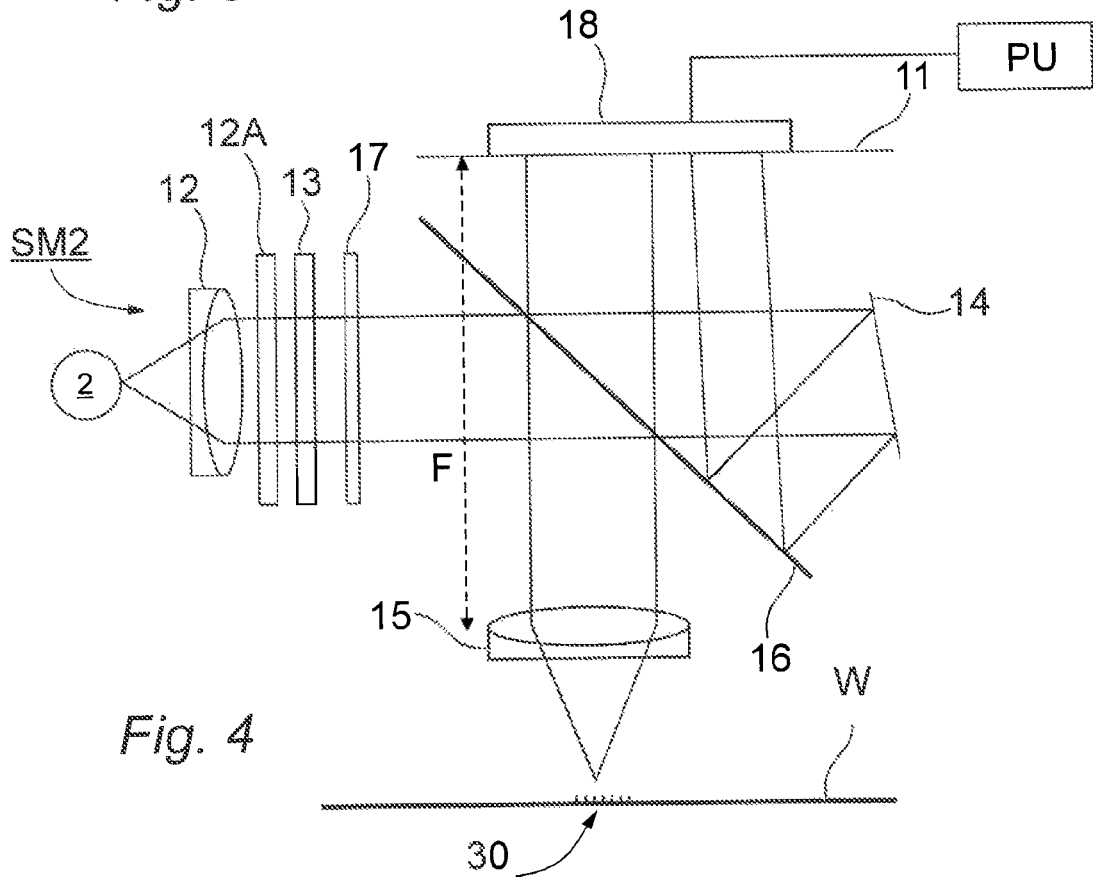
FIG. 4 depicts a second scatterometer according to an embodiment of the present invention.
Figure 5:
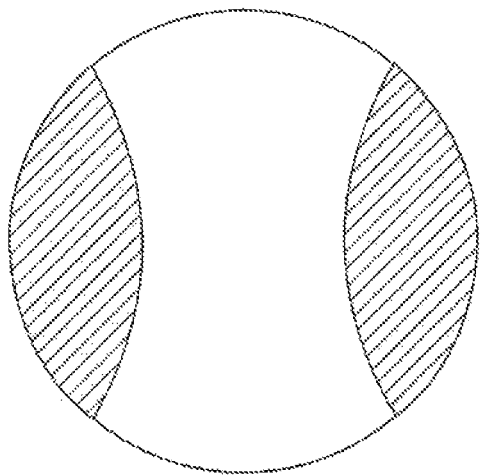
FIG. 5 depicts a pupil plane using conventional illumination.
Figure 6:
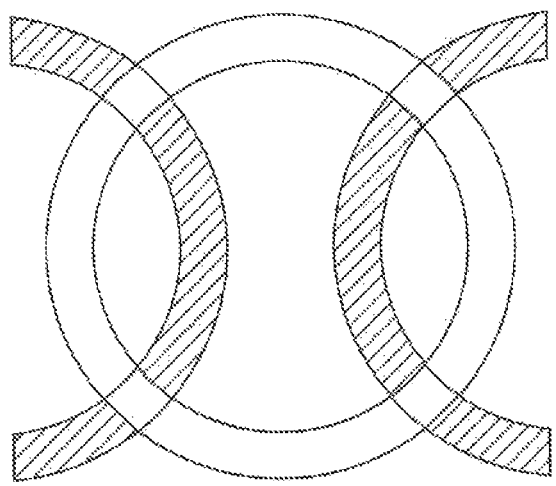
FIG. 6 depicts a pupil plane using annular illumination.

Another scatterometer that may be used with embodiments of the present invention is shown in FIG. 4. In this device, the radiation emitted by radiation source 2 is collimated using lens system 12 and transmitted through illumination aperture 12A, interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e., one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e., twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A, which is incorporated by reference herein by reference.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

An embodiment of the present invention avoids circular symmetric illumination profiles and instead uses rectangular portions of the illumination profile. Furthermore, use may be made of the rapidly decreasing intensity of higher order diffraction.

Figure 7:
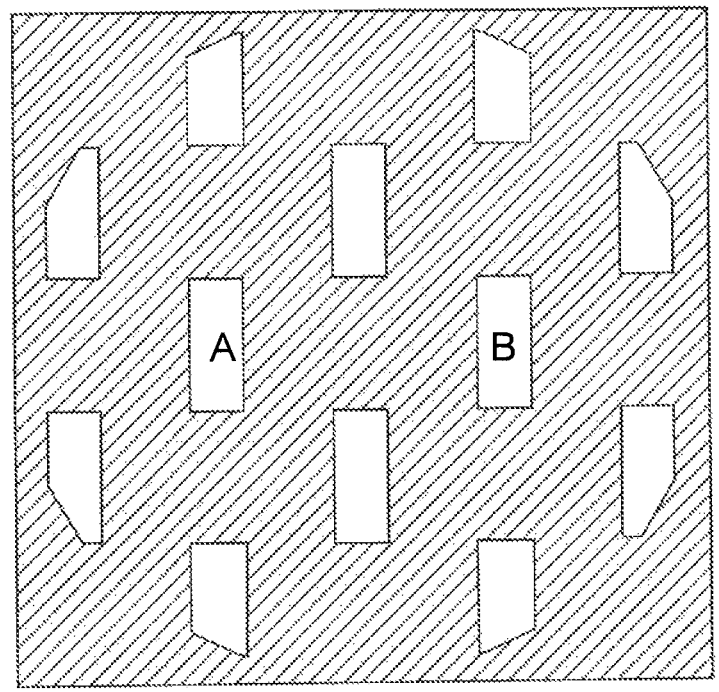
FIG. 7 depicts an illumination profile with rectangles according to an embodiment of the present invention.

The scatterometer illumination system is configured to provide a beam of radiation with an illumination profile having a plurality of illuminated portions. FIG. 7 depicts an illumination profile with rectangular illuminated portions according to an embodiment of the present invention. The rectangles, for example A and B, and the truncated rectangles at the circular perimeter of the profile boundary, are the openings in the illumination aperture.

Figure 8:
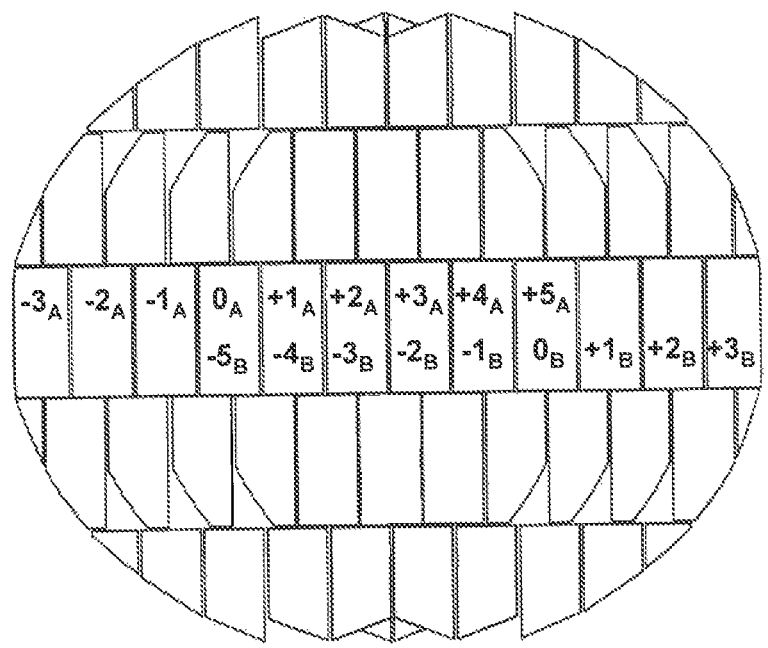
FIG. 8 depicts a pupil plane image using the illumination profile of FIG. 7.

The diffraction direction is defined as the direction at each point in the optical path that corresponds to the direction of periodicity of the target grating. The illuminated portions are separated in a direction corresponding to the diffraction direction by at least twice the spacing of the zeroth order and first order diffracted radiation in the diffraction direction. FIG. 8 depicts a pupil plane image at the detector using the illumination profile of FIG. 7. Rectangles, for example $0_A$ and $0_A$, are the areas of zeroth order specularly reflected radiation corresponding to the openings, for example A and B, in the illumination aperture. The illumination profile may be provided in other ways instead of using an aperture, such as using reflection off a micromirror array.

The detector, being a two-dimensional detector arranged in the pupil plane, is configured to separately detect the zeroth order diffracted radiation $0_A$, the first order diffracted radiation $-1_A$ and $+1_A$ and higher orders of diffracted radiation $\pm n_A$ (n=2, 3, 4, . . . ) that are distributed in the measurement plane in the diffraction direction, here horizontal.

The area of first order diffracted radiation $+1_A$ arising from illumination portion A only overlaps with area $-4_B$ which is fourth-order diffracted radiation from the target grating arising from illumination portion B. Similarly, the area of first order diffracted radiation $-1_B$ arising from illumination portion B only overlaps with area $+4_A$ arising from illumination portion A. These areas $-4_B$ and $+4_A$ results from diffraction at greater than third order which has negligible intensity at the detector. Therefore, in this example it is assumed that diffraction orders higher than third order can be neglected and consequently can overlap first orders without significantly affecting a scatterometer measurement based on detecting first orders, such as overlay or asymmetry measurements.

The plurality of illuminated portions are thus arranged such that first order diffracted radiation arising from at least one of the illuminated portions (for example A) is not overlapped by zeroth order diffracted radiation or a first order diffracted radiation arising from any other of the illuminated portions (for example B). Furthermore, the plurality of illuminated portions are arranged such that at the detector first order diffracted radiation arising from any of the illuminated portions are overlapped by at least one of the higher orders of diffracted radiation arising from any other of the illuminated portions, in this embodiment the fourth order. Also, in this embodiment the plurality of illuminated portions are arranged such that first order diffracted radiation arising from any of the illuminated portions are not overlapped by second or third order diffracted radiation arising from any other of the illuminated portions.

The processor PU (in FIG. 4) is configured to determine the property of the substrate, such as CD, side wall angle, overlay error or single grating asymmetry, from the detected radiation.

Figure 9:
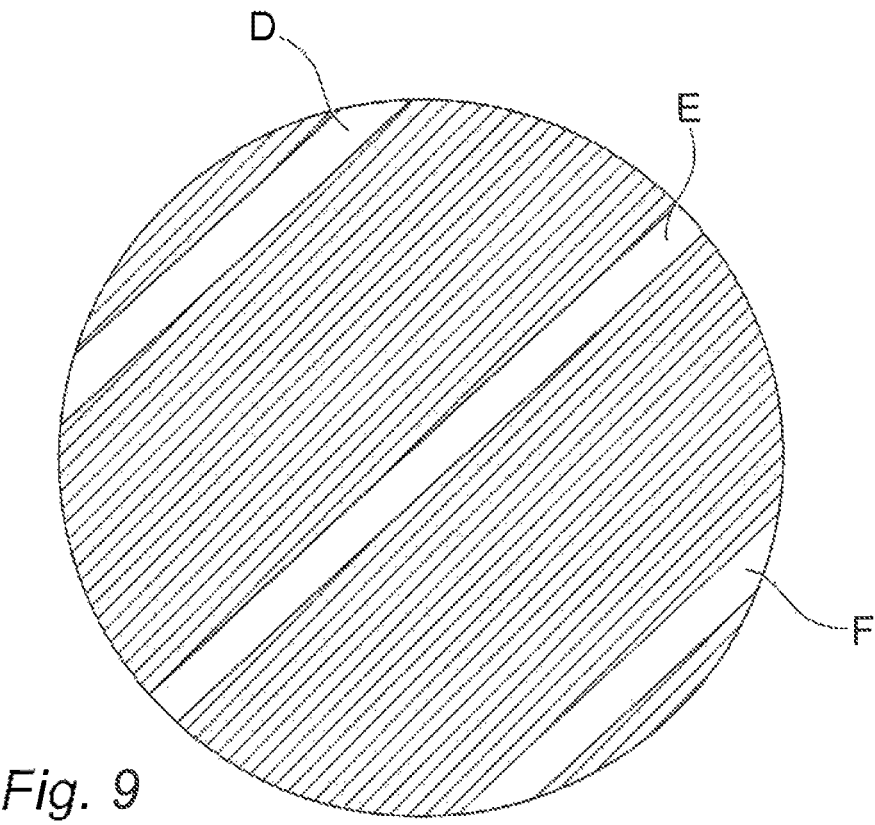
FIG. 9 depicts an illumination profile with diagonal slits according to another embodiment of the present invention.
Figure 10:
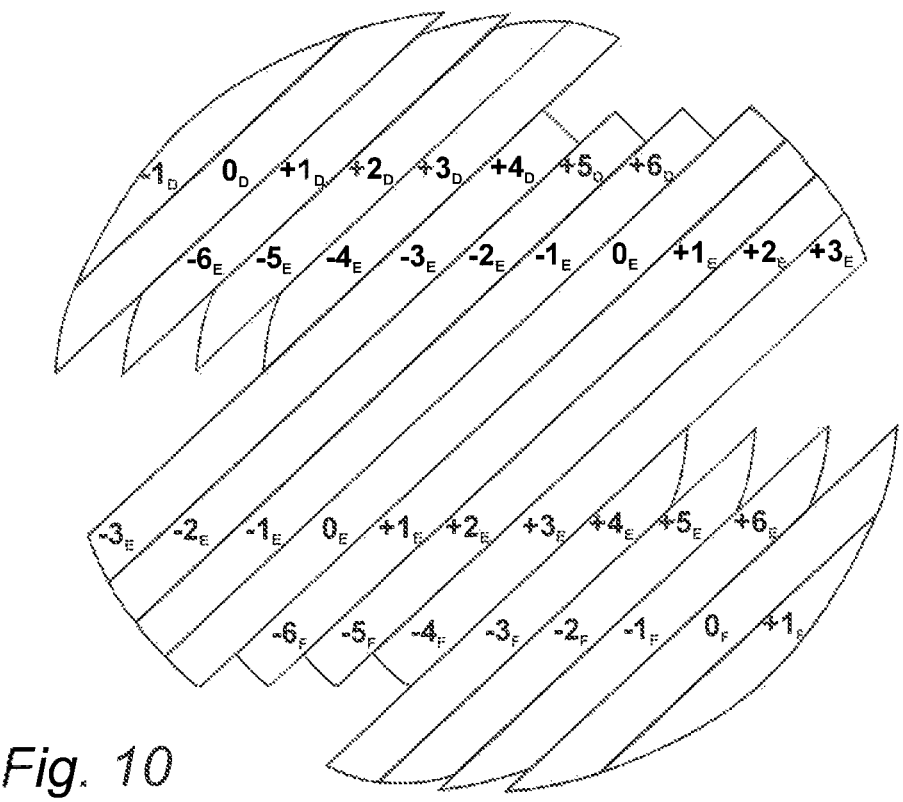
FIG. 10 depicts a pupil plane image using the illumination profile of FIG. 9 for a target grating that is periodic in the horizontal direction.

FIG. 9 depicts an illumination profile with diagonal slits according to another embodiment of the present invention. This example uses diagonal slits D, E, F in the illumination aperture. FIG. 10 depicts a pupil plane image when using the illumination profile of FIG. 9 for measuring a target grating that is periodic in the X (horizontal) direction.

In FIG. 10 $0_D$, $0_E$ and $0_F$ are zeroth order specularly reflected areas corresponding to the openings D, E and F respectively in the illumination aperture of FIG. 9. The other areas orders $\pm n_m$ (n=1, 2, 3, 4, . . . and M=D, E, F) are the respective first and higher order diffraction areas.

Figure 11:
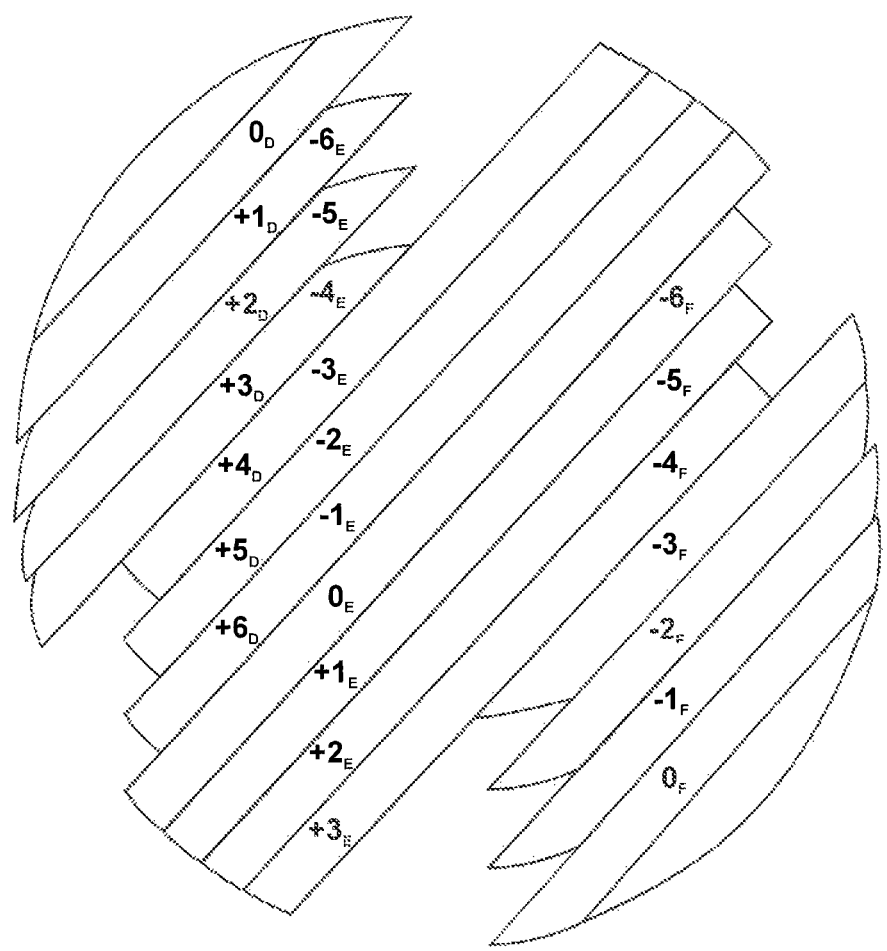
FIG. 11 depicts a pupil plane image using the illumination profile of FIG. 9 for a target grating that is periodic in the vertical direction.

The wavelength chosen in this example is 500 nm and the target grating diffracts in X direction. However, the illumination profile of FIG. 9 works equally well for diffraction in the Y direction. FIG. 11 depicts a pupil plane at the detector arising from use of the illumination profile of FIG. 9 for a target grating that is periodic in the Y (vertical) direction.

For different pitch/wavelength combinations optimization may be performed to design the illumination profile to achieve the largest area on the detector of first order diffraction from the illumination portions. The areas of first order diffraction for a given illumination portion are not overlapped by lower-than-first-order diffraction from the same or any other illumination portions.

A useful effect of the illumination profiles of both FIGS. 7 and 9 is that both normal and oblique incident light is used simultaneously.

Figure 12:
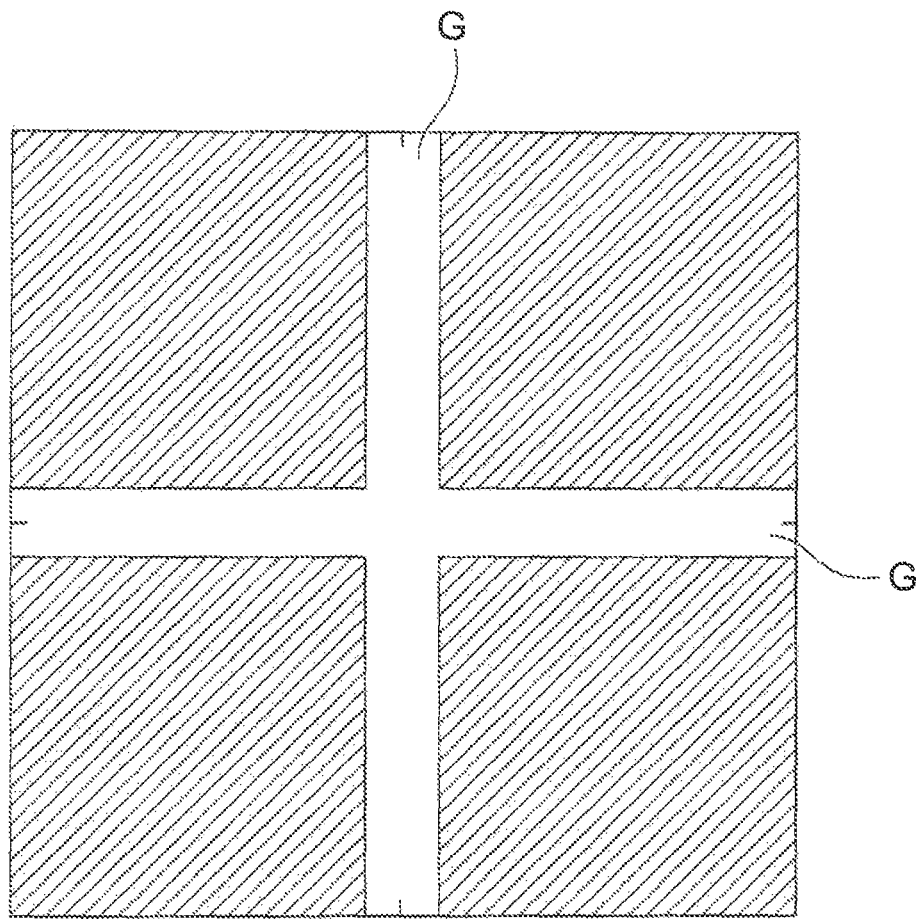
FIG. 12 depicts an illumination profile with a cross according to another embodiment of the present invention.
Figure 13:
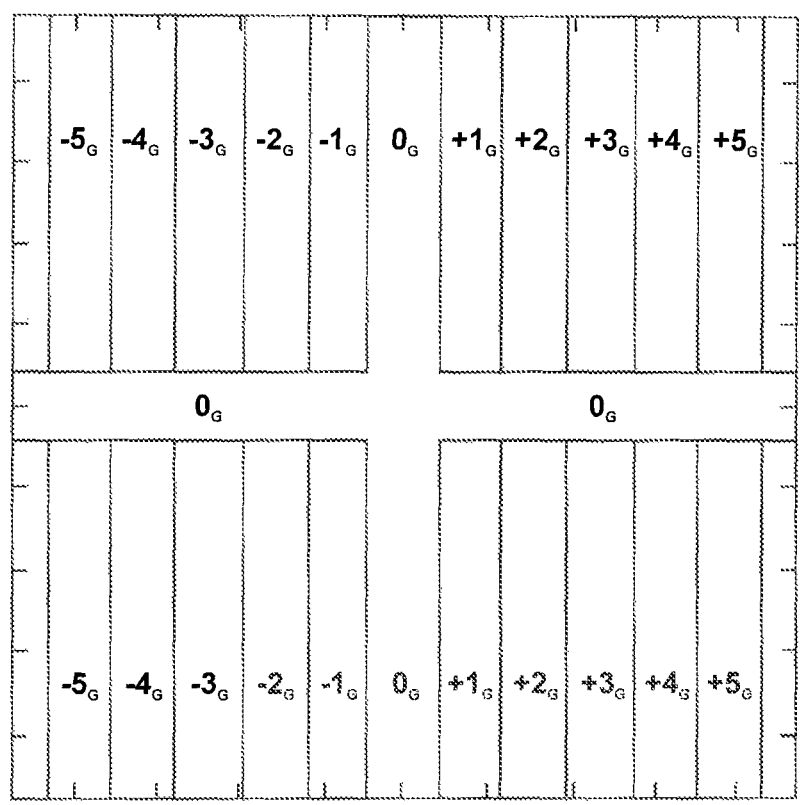
FIG. 13 depicts a pupil plane using the illumination profile of FIG. 12 for a target grating that is periodic in the horizontal direction.

Horizontal and/or vertical slit combinations can be used for the illumination profile, such as the thin "cross aperture", FIG. 12 depicts such an illumination profile with a cross according to another embodiment of the present invention. FIG. 13 depicts a pupil plane image using the illumination profile of FIG. 12 for a target grating that is periodic in the X (horizontal) direction. In this illumination profile design, outside the horizontal bar of the zeroth order cross $0_G$, higher orders do not overlap and may be separately detected for determining the scattering property, such as for overlay calculation or (asymmetry) reconstruction.

Figure 14:
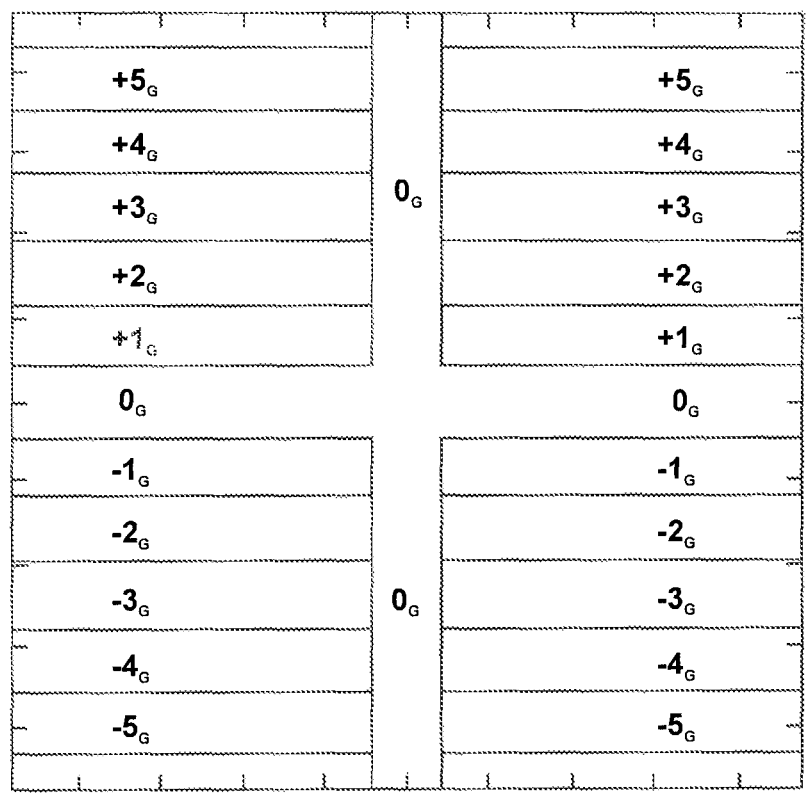
FIG. 14 depicts a pupil plane using the illumination profile of FIG. 12 for a target grating that is periodic in the vertical direction.

Here also, the aperture works equally well for diffraction in the X and Y directions. This is illustrated by FIG. 14 that depicts a pupil plane using the illumination profile of FIG. 12 for a target grating that is periodic in the Y (vertical) direction. In this illumination profile design, outside the vertical bar of the zeroth order cross $0_G$, which corresponds to the illumination portion G, higher orders do not overlap and may be separately detected for determining the scattering property.

An effect of the illumination profile of FIG. 12 is that only near-normal incidence of the illumination light is covered by this illumination profile.

In embodiments of the present invention, the scatterometer SM2 that uses the plurality of illumination portions may be incorporated into the lithographic apparatus LA of FIGS. 1 and 2.

Figure 15:
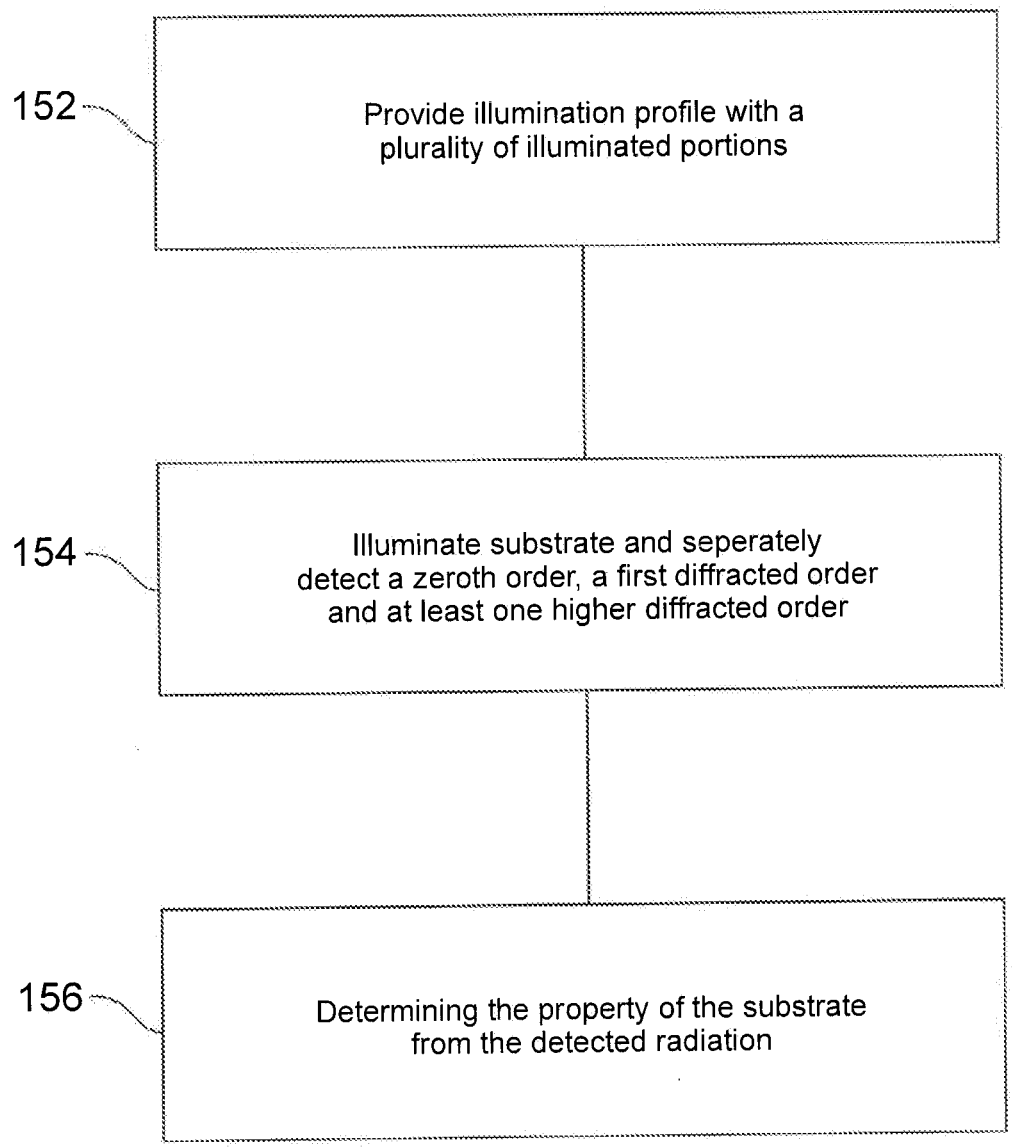
FIG. 15 is a flowchart of a method according an embodiment of the present invention.

FIG. 15 is a flowchart of a method according an embodiment of the present invention.

Step 152 is providing a beam of radiation with an illumination profile comprising a plurality of illuminated portions.

Step 154 is projecting the beam of radiation onto a periodic structure the substrate, detecting a radiation beam scattered from the periodic structure and separately detecting zeroth order diffracted radiation, first order diffracted radiation and at least one higher order of diffracted radiation.

Step 156 is determining the property of the substrate from the detected radiation wherein the illuminated portions are arranged such that detected first order diffracted radiation arising from at least one of the illuminated portions is not overlapped by zeroth order or first order diffracted radiation arising from any other of the illuminated portions.

An embodiment of the present invention performs measurements of asymmetry on single grating target, such as a large pitch alignment target or the upper or lower grating of an overlay target. The process-induced asymmetry of the alignment target or the single upper or lower grating is determined by calculating the difference in the detected plus and minus first order diffracted radiation intensity. This allows patterns of asymmetry across a wafer to be examined in a similar fashion to measured and calculated overlay errors.

Figure 16:
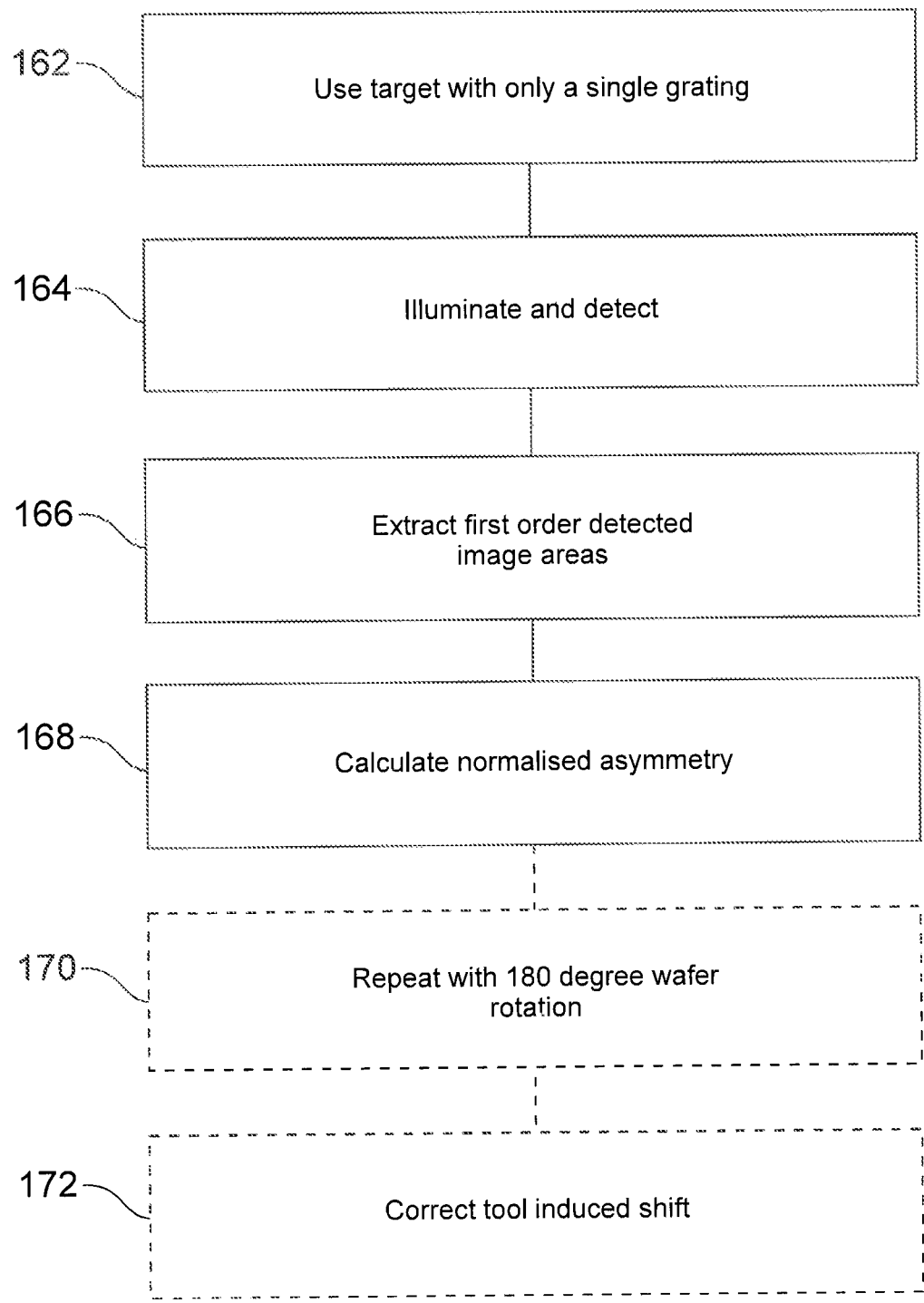
FIG. 16 is a flowchart of a method of determining single-grating asymmetry.

FIG. 16 is a flowchart of a method of determining single-grating asymmetry according an embodiment of the present invention.

In step 162 a target is produced with only a single grating for interaction with the scatterometer illumination beam.

In step 164 the target grating is illuminated. It may be illuminated with illumination profiles as described with reference to FIG. 7, 9 or 12. The spatially separated diffraction orders in the pupil plane are detected.

In step 166 the intensity of the first order areas $I^{+1}$ and $I^{-1}$ are extracted from the detector image.

In step 168 the normalized asymmetry is calculated using the formula $$A'_0 = Av\left(\frac{I_0^{+1} - I_0^{-1}}{I_0^{+1} + I_0^{-1}}\right)$$

where Av is the average over all pixels and the suffix 0 denotes the measurement with zero degrees substrate rotation.

In optional step 170, steps 164 to 168 are repeated with the wafer rotated by 180 degrees. This gives the normalized asymmetry given by the formula $$A'_{180} = Av\left(\frac{I_{180}^{+1} - I_{180}^{-1}}{I_{180}^{+1} + I_{180}^{-1}}\right)$$

where the suffix 180 denotes the 180 degree substrate rotation.

In optional step 172, the inspection tool induced shift may be corrected by taking the average of the two normalized asymmetries at 0 and 180 degree substrate rotation $$Av(A'_0, A'_{180})$$

Thus an embodiment provides a method of measuring asymmetry of a single grating periodic structure on a substrate. The method comprises (a) providing a beam of radiation; (b) projecting the beam of radiation onto the single grating; (c) detecting radiation scattered from the single grating and detecting first order diffracted radiation; and (d) determining an asymmetry of the single grating from the difference between detected positive and negative first order diffracted radiation arising from the projection of the beam of radiation.

This method may be implemented in an inspection apparatus for example by processor PU of FIG. 4 controlling the scatterometer SM2 and performing the calculations to determine asymmetry.

Figure 17:
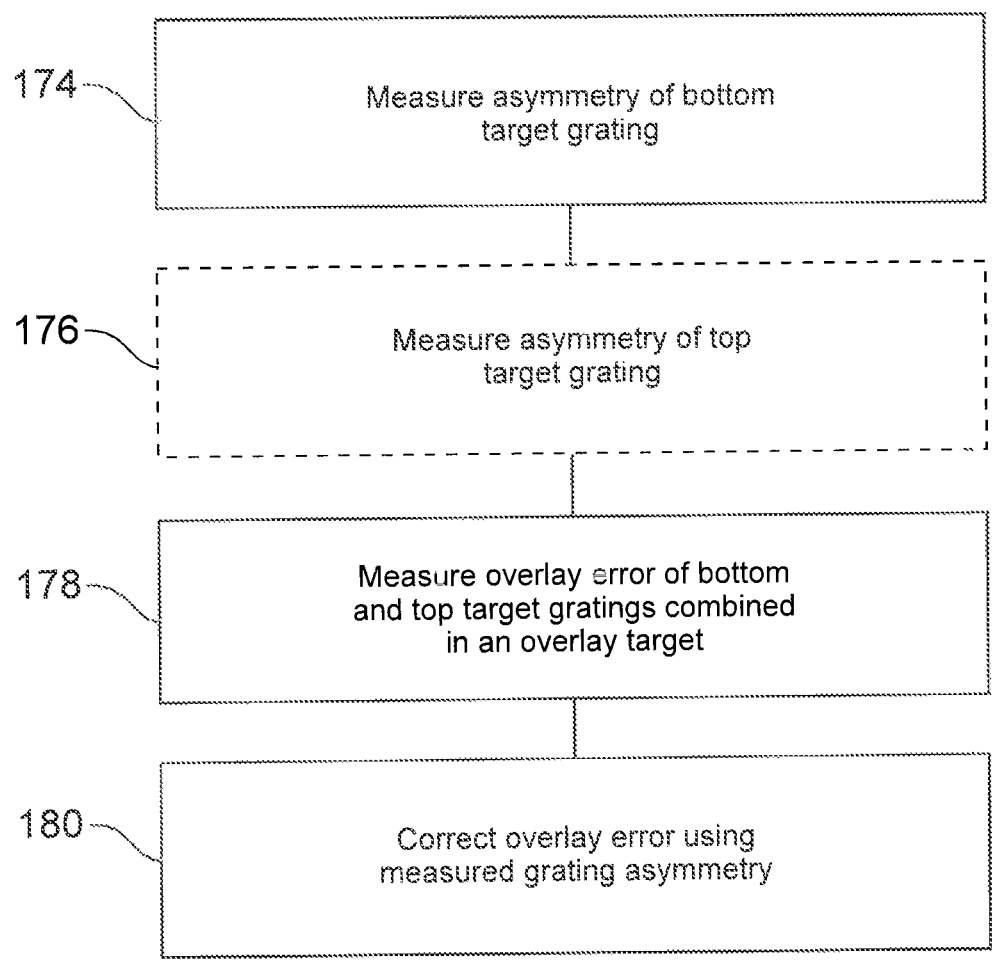
FIG. 17 is a flowchart of a method of determining overlay error using measured single-grating asymmetry.

FIG. 17 is a flowchart of a method of determining overlay error using measured single-grating asymmetry.

In step 174 the asymmetry of a bottom target grating, such as an etched grating, is measured. A first beam of radiation is projected onto bottom target grating. Radiation scattered from the single grating is detected and first order diffracted radiation is separately detected. The asymmetry of the bottom target grating is determined from the difference between detected positive and negative first order diffracted radiation arising from the projection of the first beam of radiation. This may be performed as described above with reference to steps 164 to 168, and optionally 170 to 172, of FIG. 16.

Step 174 may be performed before a top target grating, such as a resist grating, is overlaid on the bottom target grating. Alternatively, the pattering step for the resist grating may be performed to overlay the top grating on a bottom grating on the wafer, but elsewhere on the wafer, the patterning step for the top grating may be configured to leave the an area of the bottom target grating unpatterned. This bottom target area, thus unpatterned by the top grating, may then be measured in step 174.

In optional step 176, the asymmetry of the top target grating alone is measured. This step is performed on an area of the wafer where the top target grating is patterned, but where there is no underlying bottom grating target. Elsewhere on the wafer, the top grating target is patterned to overlay an area of the bottom target grating.

Usually the bottom grating, rather than the top, suffers from process-induced asymmetry. However in another embodiment, only the asymmetry of the top target grating may be measured, not that of the bottom target grating.

This stacked overlay target that combines the bottom and top target gratings is then measured in step 178. This may be performed as described above with reference to steps 164 to 168, and optionally 170 to 172, of FIG. 16 or using a method as disclosed in US Patent Publication No US2006/033921 A1, which is incorporated by reference herein in its entirety.

In step 180, which may be included in step 178, the measured overlay error is corrected using the grating target asymmetry measured in either one or both of steps 174 and 176. Due to interference between the upper and lower layers the asymmetries cannot be simply subtracted. Therefore a simulator such as one using Rigorous Coupled Wave Analysis (RCWA) may be used to apply the measured grating target asymmetry to correct the measured overlay error.

Thus an embodiment provides a method of determining overlay error of an overlay target comprising a single grating periodic structure on a substrate. The method comprises: (a) providing a first beam of radiation; (b) projecting the first beam of radiation onto the single grating; (c) detecting radiation scattered from the single grating and detecting first order diffracted radiation; (d) determining an asymmetry of the single grating from the difference between detected positive and negative first order diffracted radiation arising from the projection of the first beam of radiation; (e) providing a second beam of radiation; (f) projecting the second beam of radiation onto an overlay target comprising a pair of overlaid gratings, one of the pair being a single grating, which may for example be the same grating as measured in steps (b) and (c), or may be one processed at the same time, or using the same processing conditions as the grating measured in steps (b) and (c); (g) detecting radiation scattered from the overlay target and detecting first order diffracted radiation; (h) determining an overlay error of the overlay target from the difference between detected positive and negative first order diffracted radiation arising from the projection of the second beam of radiation; and (i) correcting the overlay error determined in step (h) using the asymmetry determined in step (d). This step may be included in step (h).

When a plurality of illumination portions are used as described in the embodiments with reference to FIGS. 7 to 11 above, then the asymmetry of the grating is determined from the difference between detected positive and negative first order diffracted radiation arising from at least one of the illumination portions.

Embodiments of the present invention provide for large pitch gratings to be efficiently measured with angle resolved scatterometers, thus enabling alignment target asymmetry reconstruction.

Embodiments of the present invention may be used in metrology tools but may also be used in scanner alignment sensors.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the present invention in the context of optical lithography, it will be appreciated that the present invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the present invention have been described above, it will be appreciated that the present invention may be practiced otherwise than as described. For example, the present invention may take the form of a computer program containing one or more sequences of machine-readable instructions describing a method as disclosed above, or a data storage medium (e.g., semiconductor memory, magnetic or optical disk) having such a computer program stored therein.

The descriptions above are intended to be illustrative, not limiting. Thus, it will be apparent to one skilled in the art that modifications may be made to the present invention as described without departing from the scope of the claims set out below.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inspection apparatus comprising:
    an illumination system configured to provide a beam of radiation forming a cross-shaped illuminated area on a periodic structure on a substrate;
    a detector configured to:
        detect radiation scattered from the periodic structure, and
        separately detect zeroth order diffracted radiation, first order diffracted radiation, and a higher order of diffracted radiation arising from the illuminated area on the periodic structure, wherein the zeroth order, the first order, and the higher order diffracted radiation are non-overlapping with each other at the detector; and
    a processor configured to determine a property of the substrate from the detected radiation.

2. The inspection apparatus according to claim 1, wherein the zeroth order and the first order diffracted radiation are non-overlapping with second order diffracted radiation arising from the illuminated area.

3. The inspection apparatus according to claim 1, wherein the zeroth order and the first order diffracted radiation are non-overlapping with third order diffracted radiation arising from the illuminated area.

4. The inspection apparatus according to claim 1, wherein the zeroth order and the first order diffracted radiation are non-overlapping with fourth order diffracted radiation arising from the illuminated area.

5. The inspection apparatus according to claim 1, wherein the detector is configured to separately detect the first order diffracted radiation and the higher order of diffracted radiation distributed in a diffraction direction corresponding to a direction of periodicity of the periodic structure.

6. The inspection apparatus according to claim 1, wherein the cross-shaped illuminated area comprises:
    a first illuminated area; and
    a second illuminated area overlapping a portion of the first illuminated area.

7. The inspection apparatus according to claim 1, wherein the cross-shaped illuminated area comprises rectangular illuminated areas.

8. The inspection apparatus according to claim 1, wherein the cross-shaped illuminated area comprises:
    a first illuminated area; and
    a second illuminated area perpendicular to the first illuminated area.

9. A lithographic apparatus comprising:
    an illumination optical system arranged to illuminate a pattern;
    a projection optical system arranged to project an image of the pattern on to a substrate; and
    an inspection apparatus comprising:
        an illumination system configured to provide a beam of radiation forming a cross-shaped illuminated area on a periodic structure on the substrate;
        a detector configured to:
            detect radiation scattered from the periodic structure, and
            separately detect zeroth order diffracted radiation, first order diffracted radiation, and a higher order of diffracted radiation arising from the illuminated area on the periodic structure, wherein the zeroth order, the first order, and the higher order diffracted radiation are non-overlapping with each other at the detector; and a processor configured to determine a property of the substrate from the detected radiation.

10. A lithographic cell comprising:

a coater arranged to coat a substrate with a radiation sensitive layer:

a lithographic apparatus arranged to expose images onto the radiation sensitive layer of the substrate coated by the coater;

a developer arranged to develop images exposed by the lithographic apparatus; and an inspection apparatus comprising:
  an illumination system configured to provide a beam of radiation forming a cross-shaped illuminated area on a periodic structure on the substrate;
  a detector configured to:
    detect radiation scattered from the periodic structure, and
    separately detect zeroth order diffracted radiation, first order diffracted radiation, and a higher order of diffracted radiation arising from the illuminated area on the periodic structure, wherein the zeroth order, the first order, and the higher order diffracted radiation are non-overlapping with each other at the detector; and
  a processor configured to determine a property of the substrate from the detected radiation.

11. A method comprising:

providing a first beam of radiation that forms a cross-shaped illuminated area on a periodic structure;

detecting radiation scattered from the periodic structure comprising a single grating; and determining an asymmetry of the single grating from a difference between detected positive and negative first order diffracted radiation arising from the illuminated area.

12. The method according to claim 11, further comprising:

providing a second beam of radiation;

projecting the second beam of radiation onto an overlay target comprising a pair of overlaid gratings, one of the pair of overlaid gratings being the single grating, detecting radiation scattered from the overlay target;

determining an overlay error of the overlay target from a difference between detected positive and negative first order diffracted radiation arising from the projection of the second beam of radiation; and correcting the overlay error based on the determined asymmetry.

13. The inspection apparatus according to claim 11, wherein the cross-shaped illuminated area comprises rectangular illuminated areas.

14. The inspection apparatus according to claim 11, wherein the cross-shaped illuminated area comprises:

a first illuminated area; and a second illuminated area perpendicular to the first illuminated area.

15. The inspection apparatus according to claim 11, wherein the cross-shaped illuminated area comprises:

a first illuminated area; and a second illuminated area overlapping a portion of the first illuminated area.

* * * * *

UNITED STATES PATENT AND TRADEMARK OFFICE
CERTIFICATE OF CORRECTION

| | | |
|---|---|---|
| PATENT NO. | : 9,235,141 B2 | Page 1 of 1 |
| APPLICATION NO. | : 13/186895 | |
| DATED | : January 12, 2016 | |
| INVENTOR(S) | : Van Der Schaar et al. | |

It is certified that error appears in the above-identified patent and that said Letters Patent is hereby corrected as shown below:

Claims

In column 17, line 8, claim 10, please delete ":" and insert --;--.

Signed and Sealed this
Tenth Day of May, 2016

Michelle K. Lee
*Director of the United States Patent and Trademark Office*